United States Patent [19]
Subbiah

[11] Patent Number: 5,353,236
[45] Date of Patent: Oct. 4, 1994

[54] HIGH-RESOLUTION CRYSTALLOGRAPHIC MODELLING OF A MACROMOLECULE

[75] Inventor: Subramanian Subbiah, Woodside, Calif.

[73] Assignee: The Board of Trustees of the Leland Stanford University, Palo Alto, Calif.

[21] Appl. No.: 872,970

[22] Filed: Apr. 23, 1992

[51] Int. Cl.$^5$ .................... G01N 23/20; G01N 23/00; G06F 15/20
[52] U.S. Cl. ..................................... 364/499; 364/496
[58] Field of Search ............... 364/499, 498, 496, 508, 364/576, 558, 413.07, 413.08, 413.09, 413.1, 413.14, 413.13; 395/157; 378/70, 71, 72, 73; 73/786, 789; 382/6

[56] References Cited

U.S. PATENT DOCUMENTS

| | | | |
|---|---|---|---|
| 5,025,388 | 6/1991 | Cramer, III et al. | 364/578 |
| 5,103,415 | 4/1992 | Omura et al. | 364/578 |
| 5,200,910 | 4/1993 | Subbiah | 364/499 |

OTHER PUBLICATIONS

Schweitz et al., *An electron statistical vacancy model for the noble metals,* (1977) J. Phys. F: Metal Phys. 8:1383-1402 No Month.

Khachaturyan et al., *The Thermodynamic Approach to the Structure Analysis of Crystals,* Acta Cryst. (1981) A37:742-754 No Month.

S. V. Semenovskaya, *Statistical Mechanics Approach to the Structure Determination of a Crystal,* Acta Cryst. (1985) A41:268-273 No Month.

S. Subbiah, *Adrift in Patterson Space,* A Proposal for the Qualifying Exam in the Harvard Ph.D. Program in Biophysics (1986) No Month.

S. Subbiah, *Low Resolution Real-Space Envelopes: An Approach to the Ab Initio Macromolecular Phase Problem,* Science 252 128-133, Apr. 5, 1991.

Primary Examiner—Jack B. Harvey
Assistant Examiner—Melanie A. Kemper
Attorney, Agent, or Firm—Hickman & Beyer

[57] ABSTRACT

A method for constructing an image of a macromolecular crystal includes steps of providing an envelope which defines the region of a unit cell occupied by the macromolecule; distributing a collection of scattering bodies within the envelope; condensing the collection of scattering bodies to an arrangement that maximizes the correlation between the diffraction pattern of the crystal and a pattern of Fourier amplitudes for the collection of scattering bodies; determining the phase associated with at least one of the Fourier amplitudes of the condensed collection of scattering bodies; calculating an electron density distribution of the crystal from the phase information; and defining an image of the macromolecule in the electron density distribution.

28 Claims, 4 Drawing Sheets

Microfiche Appendix Included
(5 Microfiche, 255 Pages)

HIGH-RESOLUTION CRYSTALLOGRAPHIC MODELLING OF A MACROMOLECULE

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

MICROFICHE APPENDIX

This specification includes microfiche Appendix A having 5 sheets with 255 frames.

BACKGROUND OF THE INVENTION

The present invention relates to the fields of crystallographic methods and apparatus for determining the three-dimensional structure of macromolecules by crystallography or electron microscopy.

Under special conditions, molecules condense from solution into a highly-ordered crystalline lattice, which is defined by a unit cell, the smallest repeating volume of the crystalline array. The contents of such a cell can interact with and diffract certain electromagnetic and particle waves (e.g., X-rays, neutron beams, electron beams etc.). Due to the symmetry of the lattice, the diffracted waves interact to create a diffraction pattern. By measuring the diffraction pattern, crystallographers attempt to reconstruct the three dimensional structure of the atoms in the crystal.

A crystal lattice is defined by the symmetry of its unit cell and any structural motifs the unit cell contains. For example, there are 230 possible symmetry groups for an arbitrary crystal lattice, while the unit cell of the crystal lattice group may have an arbitrary dimension that depends on the molecules making up the lattice. Biological macromolecules, however, have asymmetric centers and are limited to 65 of the 230 symmetry groups. See Cantor et al., Biophysical Chemistry, Vol. III, W. H. Freeman & Company (1980), which is incorporated herein by reference for all purposes.

A crystal lattice interacts with electromagnetic or particle waves, such as X-rays or electron beams respectively, that have a wavelength with the same order of magnitude as the spacing between atoms in the unit cell. The diffracted waves are measured as an array of spots on a detection surface positioned adjacent to the crystal. Each spot has a three-dimensional position, hkl, and an intensity, I(hkl), both of which are used to reconstruct the three-dimensional electron density of the crystal with the so-called Electron Density Equation:

$$\rho(x, y, z) = \frac{1}{V} \sum_{h,k,l=-\infty}^{\infty} F(h, k, l) \exp[-2\pi i(hx + ky + lz)]$$

where $\rho(x,y,z)$ is the electron density at the position (xyz) in the unit cell of the crystal, V is the volume of the unit cell, and F(h,k,l) is the structure factor of the detected spot located at point (h,k,l) on the detector surface. As expressed above, the Electron Density Equation states that the three-dimensional electron density of the unit cell is the Fourier transform of the structure factors. Thus, in theory, if the structure factors are known for a sufficient number of spots in the detection space, then the three-dimensional electron density of the unit cell could be calculated using the Electron Density Equation.

A number of problems exist, in actual practice, however. The Electron Density Equation requires knowledge of the structure factors, F(h,k,l), which are generally complex numbers that consist of both an amplitude and a phase. The amplitude of a structure factor, |F(h,k,l)|, is simply the square root of the experimentally measured intensity, I(h,k,l). The phase of each structure factor, on the other hand, is not known and cannot be measured directly in a diffraction experiment. Nor can it be derived directly for macromolecules. Without the phase of each structure factor, determination of the three-dimensional structure of most large structures by the use of the Electron Density Equation is impossible except for special cases.

Theoretical methods are exemplified by the Direct Method and the Patterson Method or their extensions, as well as the maximum entropy method or the use of simulated annealing in both reciprocal and Patterson space. These methods calculate the phases directly from the measured intensities of the diffracted waves and allow routine computer solutions for molecules having typically less than approximately 100 non-hydrogen atoms. (As is known in the art of crystallography, hydrogen atoms contribute little to the diffraction process.) For structures having more than 100 non-hydrogen atoms, such as proteins, peptides, DNA, RNA, virus particles, etc., such direct methods become impractical and, in most cases, impossible. Fortunately, experimental methods, such as Multiple Isomorphous Replacement and Anomalous Scattering, exist to aid in the determination of these phases.

Multiple Isomorphous Replacement is based on the observation that the absolute position and, therefore, the phase of the structure factor of a heavy-atom incorporated into an otherwise unmodified crystal lattice can be determined. With this knowledge, the phase of each structure factor in the derivative is determined relative to that of the heavy-atom. Except for crystals having centrosymmetric symmetry, at least two heavy metal derivatives are required to unambiguously determine the phase of a structure factor. Furthermore, Multiple Isomorphous Replacement requires that each heavy metal derivative does not otherwise change the structure of the molecule, or distort the unit cell of the crystal.

Other experimental techniques, used in conjunction with Multiple Isomorphous Replacement allow the crystallographer to forego analysis of some heavy metal derivatives. One such technique, Anomalous Scattering, is based on the observation that particular heavy-atoms scatter radiation of different wavelengths significantly differently. With this technique, one heavy metal derivative studied at two wavelengths yields data equivalent to two heavy-atom derivatives studied at one wavelength.

Other techniques completely circumvent the preparation and study of heavy metal derivatives- For example, molecular replacement, as the name suggests, uses a molecule having a known structure as a starting point to model the structure of the unknown crystalline sample. This technique is based on the principle that two molecules that have similar structures and similar orientations and positions in the unit cell diffract similarly. Effective use of this technique requires that the structures of the known and unknown molecules be highly homologous.

Molecular replacement involves positioning the known structure in the unit cell in the same location and orientation as the unknown structure. Difficulty in using this technique arises because the result is critically dependent on the exact positioning of the known structure. Slight variations in either the location or orientation of the known structure often results in complete failure. Once positioned, the atoms of the known structure in the unit cell are used in the so-called Structure Factor Equation to calculate the structure factors that would result from a hypothetical diffraction experiment. The Structure Factor Equation takes the form:

$$F(h, k, l) = \sum_{j=1}^{N} f_j \exp[2\pi i(hx_j + ky_j + lz_j)]$$

where F(hkl) is the structure factor of the molecule at the point (hkl) on the detector surface, $f_j$ is the atomic structure factor (that is, it represents the scattering properties of the individual atom), N is the number of non-hydrogen atoms, and $x_j, y_j, z_j$ are the fractional coordinates of atom j in the unit cell. The structure factor calculated is generally a complex number containing both the amplitude and phase data for the molecular replacement model at each point (hkl) on the detector surface. These calculated phases are used, in turn, with the experimental amplitudes measured for the unknown structure to calculate an approximate electron distribution. By refinement techniques, this approximate structure can be fine-tuned to yield a more accurate and often higher resolution structure.

The molecular replacement technique requires knowledge of the number of molecules, and the orientation and position of each molecule within the unit cell. Initially the electron density calculated from the phases from the molecular replacement model and experimental amplitudes closely resembles the electron density of the model. Only after refinement of the initial structure will the success or failure of the method be apparent. For instance, failure occurs if the initial structure fails to converge (as represented by a correlation value) or if the refined structure diverges from the structure of the model during the refinement process. In cases where the unknown structure is a substrate or intermediate bound to a protein, molecular replacement's success is evident when the result is a structure whose only difference is added electron density that represents the protein-bound molecule. The determination of such structures is important in the area of pharmaceutical drug testing where the structure of protein-bound drugs and intermediates yield important information about binding and mechanism. Similarly, new mutants of a protein or variations of protein-bound inhibitors are well suited for molecular replacement, as are structures of the same molecule that have crystallized in different symmetry groups.

Molecular Replacement is not always effective, however. Determination of the number of copies of the model in the asymmetric unit and the correct location and orientation of each copy is critical and time consuming, since ideally one samples all rotational and translational degrees of freedom in the asymmetric unit to determine the correct set of parameters.

Recently, S. Subbiah has reported an ab initio approach for obtaining the low-resolution envelopes of certain macromolecules, (S. Subbiah, Science (1991) Vol. 252, pp. 128–133 which is incorporated herein by reference for all purposes). In this method, a collection of hard-sphere point scatterers is permitted to move randomly and ultimately find an arrangement corresponding to the image of the macromolecule or the surrounding solvent. The details of this technique are discussed in U.S. application Ser. No. 831,258 (attorney docket number 5490A-80-1, filed Jan. 30, 1992) which is incorporated herein by reference for all purposes. Unfortunately, this technique has not been extended to high-resolution results, and is typically limited to results having a resolution in the range of 10 to 15 Å.

Because Multiple Isomorphous Replacement, Molecular Replacement, and their related techniques do not work for all cases, there exists a need for simplified, efficient methods to determine the high-resolution structure of crystalline molecules. The present invention fulfills these and other needs.

SUMMARY OF THE INVENTION

The present invention produces a high-resolution model of the electron density distribution of a macromolecule in a defined asymmetric unit of a crystal lattice. This is accomplished through a simple and rapid method for determining the phases of the reflection data for the macromolecule of interest. The process is started with a low-resolution envelope of the macromolecular crystal. That envelope is used to obtain the phase of the structure factor for one (or a few) low-resolution reflection. The phase of that structure factor is then used to construct a new, higher resolution, envelope which is, in turn, used to calculate the phase for a higher resolution reflection so that an even higher resolution envelope can be constructed. In this manner, the resolution of the envelope is improved by bootstrapping the solution from earlier calculations and the diffraction data. The process can be terminated at any stage, regardless of resolution. Thus, if the desired resolution is only intermediate, the process of this invention can be terminated after the diffraction data of intermediate resolution has been phased.

In one aspect, the present invention is directed to a method for constructing an image of a macromolecule crystal with the aid of a digital computer and an experimental diffraction pattern for the crystal. First, an envelope defining the region of a unit cell occupied by the macromolecule is provided. Within that envelope a collection of scattering bodies is distributed in a particular arrangement. These scattering bodies have an associated pattern of Fourier or scattering amplitudes that can be calculated by a variety of methods, including the structure factor equation. The collection of scattering bodies is then condensed to an arrangement that maximizes the correlation between the experimental diffraction pattern and the pattern of the Fourier amplitudes for the collection of scattering bodies. At this point, the phase associated with at least one of the diffraction pattern reflections can be determined and used to calculate the electron density distribution corresponding to that phase or a few phases of the macromolecule crystal. Finally, an image of the macromolecule crystal for this or these few phases can be obtained from the electron density distribution by, for example, identifying a contour on the distribution that encompasses a percentage of the unit cell corresponding to the percentage actually occupied by the macromolecule.

According to a preferred embodiment of the invention, the scattering bodies are condensed in the following manner. Data is collected from a diffraction experiment of a crystal lattice, inputted into a computer, and converted into normalized amplitudes. A collection of scattering bodies is distributed in an envelope within an asymmetric unit having the same dimensions as a true asymmetric unit of the crystal lattice. The scattering amplitudes and phases of the initial distribution are then calculated, and the correlation between the calculated scattering amplitudes and the normalized amplitudes is calculated to determine the fit between the two data sets. At least one of the scattering bodies within the envelope is moved to create a modified distribution, the scattering amplitudes of this modified distribution are calculated, and the correlation between the calculated amplitudes and the normalized values is recalculated- A final distribution of scattering bodies is produced by repeating the process of moving at least one of the scattering bodies to create a modified distribution and determining the correlation between the calculated amplitudes and the normalized values, until the correlation between the calculated scattering amplitudes and the normalized amplitudes is effectively maximized. This final distribution of scattering bodies defines the condensed arrangement of the scattering bodies within the specified envelope.

Another aspect of the present invention provides a method for determining the location of heavy-atoms in a heavy-atom derivatized macromolecule. To utilize this method, diffraction patterns for both the hearty-atom derivatized macromolecule and for the corresponding underivatized version of the macromolecule are necessary. The method described above is then used to obtain the phases of selected reflections of the underivatized macromolecule. These phases are saved for later use. Next, an amplitude difference for each structure factor is determined by subtracting the amplitudes of the structure factors for the underivatized macromolecule from the corresponding amplitudes of the structure factors for the heavy-atom derivatized macromolecule. These amplitude differences are combined with the corresponding saved phases from the underivatized macromolecule to obtain structure factor differences for selected reflections. Finally, the structure factor differences, which have both phase and amplitude information, are used to produce an electron density distribution of the heavy-atoms. This distribution will show both the number of heavy-atoms and their locations on the macromolecule.

A further understanding of the present invention may be obtained by referring to the following discussion, figures, and associated examples.

BRIEF DESCRIPTION OF THE DRAWINGS

FIG. 1b is a schematic representation of the detection plate of FIG. 1a;

DESCRIPTION OF THE PREFERRED EMBODIMENT

Table of contents

Figure 1A:
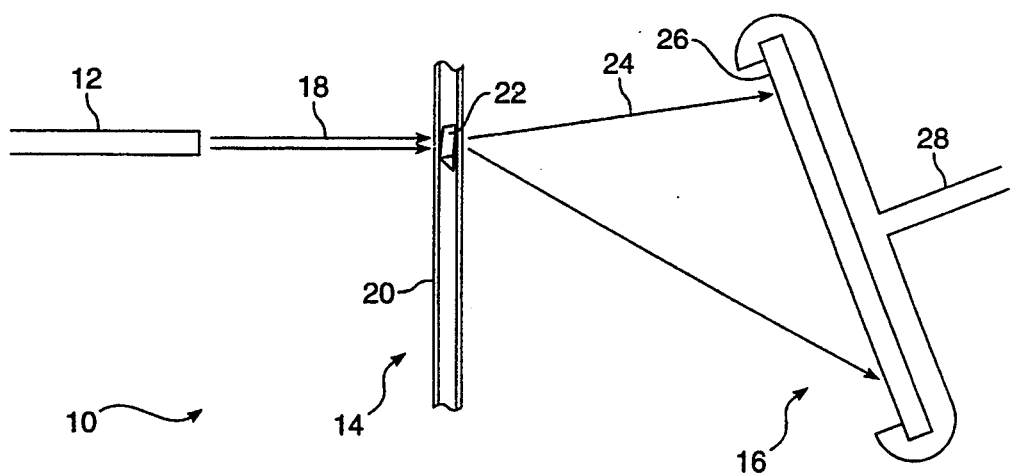
FIG. 1a is a schematic drawing of an X-ray diffractometer.

I. Overview
II. Data Collection and Manipulation
III. Salient Features and Initial Procedures
IV. Initial Distribution of the Scattering Bodies
V. Condensing Protocol for Phase Extraction
VI. Extracting Phases for Structure Factors
VII. Refining Higher Resolution Envelopes
VIII. Examples
IX. Other Embodiments The present invention will be described by providing details of each procedure involved in the modelling procedure.

I. Overview

When macromolecules crystallize, solvent typically occupies large portions of the crystal lattice. The bulk of the solvent incorporated with the macromolecule is fluid and consists of randomly oriented molecules that do not diffract X-rays, electron beams, neutron beams, and the like. The portion of the unit cell occupied by the macromolecule is termed the "positive image," while the portion occupied by solvent is termed the "negative image." The term "macromolecular envelope" denotes the surface of the macromolecule (i.e. the boundary between the solvent and the macromolecule) as defined at a particular resolution. A high-resolution macromolecular envelope includes many detailed features of the macromolecular surface, such as location of side chains, clefts, etc. Conversely, a low-resolution envelope only provides details about the general shape of the macromolecule. Putting this in more quantitative terms, at 2 Å resolution, the atoms of the macromolecule can be seen, at 3 Å resolution peptide side chains can been seen but not easily distinguished, at 4 Å resolution peptide helices and beta sheets can be seen, and at 5.5 Å only peptide helices can be distinguished. Typically, availability of a good 4 Å resolution envelope can allow the structure to be easily and completely determined by means of two current methods—tracing and refinement—that are well known in the art. Further, the same methods can frequently, but with more difficulty, allow complete determination of the structure from a good 5 Å or 5.5 Å resolution envelope.

The term "macromolecule" includes, but is not limited to the following general types of compounds: biological macromolecules such as proteins, peptides, RNA, DNA, complexes of peptides and nucleic acids, virus particles, organelles, and the like; organic molecules such as organic polymers, plastics; inorganic molecules such as zeolites; and other large molecular structures. Although the term "protein" is used below in conjunction with the description of illustrative embodiments, the method is fully suited for structure determination of other macromolecules that crystallize into a unit cell having solvent space.

Preferred methods of this invention include various procedures such as (1) collecting diffraction data; (2) inputting experimental crystallographic data into a computer which is used to perform the method; (3) distributing scattering bodies in a corresponding asymmetric unit envelope; (4) condensing the scattering bodies by repeatedly moving the scatters to maximize the correlation between the experimental and calculated data; (5) determining phases of some structure factors from the condensed scattering bodies; (6) generating a new, higher resolution envelope from the phase data; and (7) moving a new group of scatterers within the new envelope until the correlation with the experimental data is maximized.

II. Data Collection and Manipulation

Collection of diffraction data from scattered waves is well known in the art of crystallography. Referring to FIG. 1a, a diffractometer 10 (also known as an X-ray set) for use with the present invention includes a source of X-rays 12, a sample holder 14, and a detection apparatus 16. X-ray source 12 produces a collimated beam 18 of X-rays having a relatively narrow cross section. Suitable x-ray sources include mercury flash tubes, copper cathodes and rotating anodes that produce X-rays having a narrow and well-defined wavelength spectrum.

In other preferred embodiments, alternate forms of radiation and radiation sources are used. For example, an alternate source of X-rays, such as a tunable X-ray source (e.g., radiation from a synchrotron or other source that emits X-rays of different wavelengths) is preferred for use with techniques such as Anomalous Scattering or Multiple Wavelength Scattering. Alternate forms of radiation include electron beams (e.g., those typically used in electron microscopy), neutron beams (e.g., those typically used in neutron beam diffraction), and the like.

Sample holder 14 consists of a capillary tube 20 having a crystallized sample 22 located within its lumen. Capillary tube 20 and crystallized sample 22 are positioned in the path of collimated X-ray beam 18. X-rays 24 diffracted by the crystal impinge on a detection apparatus 16 that is positioned generally opposite X-ray source 12 and that consists of a detector surface 26 mounted on an arm 28. Detection surface 26 takes on many shapes, such as a two-dimensional disk, a three-dimensional cylindrical surface, and the like, and is adapted to record the position and intensity of diffracted X-rays 24. Examples of suitable detection surfaces for use in the present invention include photographic film, gas chamber or multi-wire area detectors, CCD channel plates, image plates, diffractometers including precession cameras, and the like. In many apparatus, e.g., a precession camera, the rotation of sample holder 14 and detector surface 26 are coupled during the diffraction experiment to accumulate data corresponding to an entire plane in reciprocal space (i.e., the space of hkl reflections).

Figure 1B:
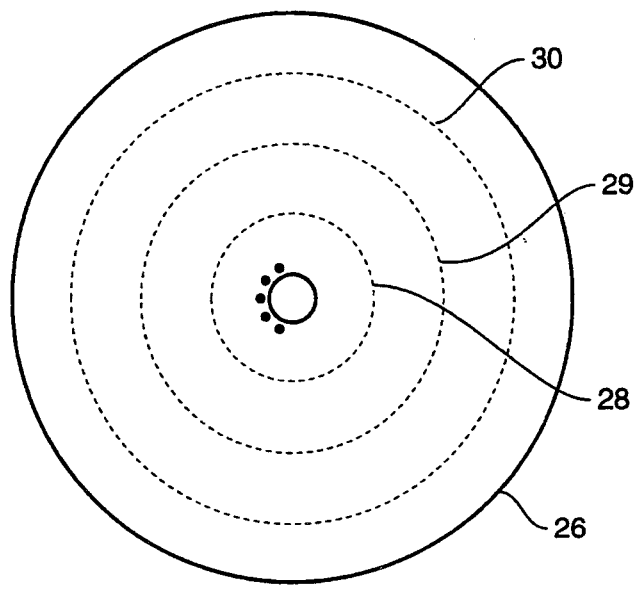

Referring now to FIG. 1b, detector surface 26 after exposure to diffracted X-rays consists of an array of spots that each have a position, (hkl), and an intensity, I(hkl). The data form an array having a circular boundary 30 that represents the high-resolution limit of the diffraction experiment. Data representing low-resolution features of the crystal are located near the center of the circular array while data representing the high-resolution features are near the outer edge. For example, data lying within the circle defined by circle 27 represent lower resolution features of the crystal (e.g., down to 10 Å), while data lying between circles 29 and 30 represent features of higher resolution (e.g., between 2 Å and 5 Å).

Low-resolution data is sometimes not recorded because it is produced at high intensities capable of damaging some detectors (or the film on which the diffraction pattern is recorded). For purposes of this invention, however, much of the low-resolution data could be recorded and can be easily recorded using appropriate detectors, such as the Nicolet diffractometers. In particular, complete data from reflections lower than the 50th reflection should be recorded. More preferably, complete data from reflections lower than the 100th reflection (and most preferably lower than the 200th reflection) should be recorded.

During a diffraction experiment, data collection typically involves accumulation of a large number of data points, often over 10,000. After accumulation on an appropriate detection surface the position and intensity of each data point is measured, as is known in the art of crystallography, and the data are put into a computer for storage and further processing. In a preferred embodiment, the computer is a digital computer such a VAX 8550, produced by Digital Equipment Corporation of Maynard, Mass. Other computers of varying computational power are also suitable: supercomputers, multiprocessor computers, mainframe computers, work stations, personal computers, and the like. Exemplary computers for use with the present invention include computers produced by Cray Research, Digital Equipment Corporation, Thinking Machines, Data General, International Business Machines, Apple Computer, Sun Computers, and Silicon Graphics. In other embodiments special duty computers are used. For example, an appropriate digital computer incorporated into a diffractometer is suitable for performing the invention method.

Figure 1C:
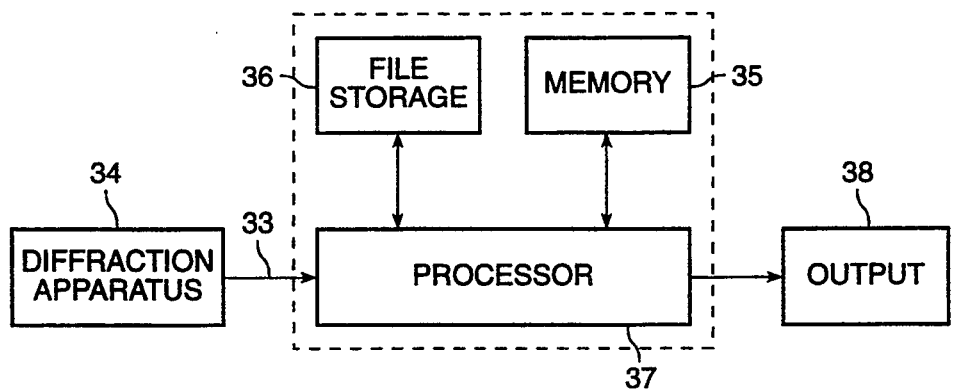
FIG. 1c is a block diagram illustrating the computer hardware to which the invention may be applied.

Referring now to FIG. 1c, a computer 32 used in conjunction with the present invention includes an interface 33 to receive data from a diffraction apparatus 34, memory 35 (e.g., RAM), file storage 36 (e.g., magnetic disk or tape) to store the data, and a CPU 37 to process the data. In preferred embodiments, the computer further includes an output device 38, such as a printer, plotter, or graphics display, that allows the resulting electron density of the crystal to be displayed graphically. Typical graphic displays are produced by Evans and Sutherland. Computer coding (phasol_condense.f, Fortran) that has been used to implement the present invention is attached hereto as Appendix A. To use this coding, the main routine is compiled together with the subroutines presented in Appendix A.

The crystallographic symmetry and dimensions of the unit cell and asymmetric unit are all determined directly from the data (see Blundell and Johnson "Protein Crystallography" Academic Press, N.Y. 1976, which is incorporated herein by reference for all purposes). The unit cell is the smallest portion of the crystal lattice that repeats upon operation of a translation. Thus, determining the electron density of the unit cell is equivalent to determining the electron density of the crystal lattice. In most space-groups, the unit cell has multiple copies of the crystallized macromolecule, and may have internal symmetries, such as an n-fold rotation axis, etc., termed "crystallographic" symmetries. Subspaces of the unit cell that are related by such crystallographic symmetries, are termed "asymmetric units." Determining the electron density of the asymmetric unit is also equivalent to determining the electron density of the crystal lattice because the unit cell can be constructed from the asymmetric unit by applying the appropriate symmetry operations. When the unit cell has no internal symmetry, the asymmetric unit is the same as the unit cell. In other crystals, for example, the asymmetric unit may be half of the unit cell or less.

Once the symmetry and dimensions of the asymmetric unit are determined, the experimental data are converted from unscaled F-values (i.e. the magnitude of the structure factor or the amplitude associated with I(h,k,l)) into a form convenient for use in the method of the present invention. In a preferred embodiment, a portion of the experimental data are converted into normalized structure-factor magnitudes (i.e., E-values) that are conventionally used in Direct Methods (See Karle, *Acta Crystal.* 1989, vol. A45, pp. 765–781, which is hereby incorporated by reference for all purposes). As used herein, "portion" is used to indicate a subset or the whole of the experimental data, since some cases require conversion of the entire data set, while others require conversion of a subset. While F-values represent scattering by atoms that have a finite electron distribution, normalized E-values represent scattering by bodies that have no spatial distribution and have a simple scattering cross-section. Thus, this conversion models the crystal as an array of point scatterers rather than atoms. Alternatively, the accumulated data is converted into properly scaled F-values, as described in Blundell and Johnson. The use of properly scaled F-values or normalized E-values depends on the details of the calculations. In a preferred embodiment, E-values are used in conjunction with high-resolution data. With data having resolutions lower than approximately 8 Å, however, either F-values or normalized E-values are used (with a corresponding change in the Electron Density and Structure Factor Equation as is well known in the art) with no substantial difference in the results. In ensuing discussions, therefore, properly scaled F-values and normalized E-values are used interchangeably at lower resolutions unless otherwise specified, and are collectively referred to as "experimental data."

Once diffraction data are collected and converted to properly scaled F-values or normalized E--values, and the crystallographic symmetry and dimensions of the asymmetric unit have been determined, the electron density of the crystal is modelled. This is accomplished at successively higher resolutions by alternately condensing an arrangement of point-scatterers to maximize correlation with experimental data, and back-calculating the Fourier phases from the condensed distribution of scatterers. Thus, a higher-resolution description of the macromolecule structure is boot-strapped from lower resolution results.

III. Salient Features and Initial Procedures

To conduct the method of the present invention, all that is required is X-ray diffraction data for the macromolecule of interest and apparatus for calculating and displaying the structural results. Preferably, all reflections typically collected, as well as most of the lowest 50 reflections, will be used in this method. More preferably, complete sets of the lowest 100, and most preferably the lowest 200 reflections will be used with the higher resolution reflections normally collected. Because these low-resolution reflections typically produce a much higher intensity image than the higher resolution reflections, they are sometimes not recorded in conventional X-ray diffraction experiments. However, they may easily be recorded from even poor crystals in less than an afternoon's time with a Nicolet diffractometer that is generally used in conjunction with small molecule crystallography.

The present invention provides a stepwise method by which the resolution of a macromolecular image is gradually increased by using successively higher resolution reflections from the experimental data. Thus, if only intermediate resolution is required for the task at hand, the method can be terminated after sufficient resolution is attained. If, however, a high-resolution structure is required, the method can be stepped to its full potential, providing images that are suitable for tracing and even atomic resolution. As is known in the art, different techniques can be used in series or parallel to arrive at the desired structure. Thus, for example, the present invention could be used in conjunction with traditional techniques such as, for example, (1) molecular replacement with full or partial models; (2) phase extension based on three- or more fold non-crystallographic symmetry; (3) available high-resolution SIR data; (4) two dimensional electron microscopy, where Fourier data are typically of higher resolution than the available direct phases; or (5) verification of suitable heavy-atom candidate data sets.

Each series of procedures used to obtain a new macromolecular envelope is termed a phase walk step, or "PW step." Although each new envelope will generally have a higher resolution than the previous envelope, certain procedures are common to all PW steps. These include (1) condensation of scattering bodies, (2) back calculation of phases of the structure factors, (3) generation of an electron density map, and (4) selection of map contours to define a macromolecule envelope. Some of these procedures will vary slightly from PW step to PW step as will be described below.

Errors should be minimized throughout the procedure. If they are introduced in the early, low-resolution PW steps, they will propagate as the macromolecular envelope is refined to a high-resolution structure, thus corrupting the final results. The calculations should therefore, to the extent necessary, be carefully controlled at each PW step. This may be accomplished by, for example, calculating the phase for only a single reflection at each new PW step, especially at the low-resolution PW steps. If the calculated phase appears incorrect for any given reflection, that reflection's contribution to the solution may be reduced or eliminated. When too many reflections are phased at one time, it is difficult to identify the reflection(s) responsible for the error. Nevertheless, at higher resolution PW steps, when the detailed structure is nearly complete, it may be desirable to phase several reflections at one time to expedite the procedure.

To begin the method of this invention, a low-resolution image of the macromolecule is necessary. This image should merely describe the general boundaries (or envelope) of the macromolecule, as distinguished from the solvent, within the asymmetric unit. It need not resolve helices, sheets, clefts, or other large features. Rather, it defines a domain within which initial calculations are performed to obtain the phase of the structure factor for the lowest resolution reflection or lowest 3 or 4. For higher resolution reflections, more accurate envelopes will be necessary, as explained below. But because the lowest resolution reflections are commonly centric (and therefore have phases restricted to one of either 0° or 180° as is well-known in the art), phases can be extracted more easily. Thus, a slightly erroneous calculated phase may be simply rounded off to 0° or 180°.

A suitable low-resolution image for use in obtaining the first envelope can be obtained by the method disclosed in U.S. patent application Ser. No. 831,258 and in S. Subbiah, *Low-Resolution Real-Space Envelopes: An Approach to the Ab Initio Macromolecular Phase Problem,* Science, 252 128–133 (1991), both of which were previously incorporated herein by reference for all purposes. Alternatively, an image of this resolution can easily be derived from electron microscopy, electron crystallography, neutron diffraction, etc.

For many of the low-resolution envelopes calculated as suggested above, some regions of the "true" protein will erroneously fall outside of this envelope, and some regions outside the domain of the protein will fall within the envelope. For purposes of this invention, however, the envelope should completely surround the region occupied by the true protein, leaving no region of the protein protruding beyond the envelope. Thus, in many instances, it will be necessary to "expand" the boundaries of the low-resolution image to, for example, twice their original size to allow for possible sources of minor error in the available envelope. If the low-resolution image is provided in the form of an electron density map, it can be expanded by simply choosing its boundaries to be the region circumscribed by a relatively low electron density contour. Other methods for expanding the size of the image will be apparent to those of skill in the art. Of course, when the "unexpanded" image is known to be overly large, no expansion procedure may be necessary.

After the initial envelope is defined, the sequence of substeps listed above (e.g. distributing scattering bodies within the envelope, etc.) is conducted to complete the PW step and produce a higher resolution envelope. This new envelope is then used with the same series of substeps to produce an even higher resolution envelope. This process is continued until an envelope of the desired resolution is produced. As noted the substeps used in each PW step are substantially the same. Thus, the following discussion can, unless otherwise noted, be applied to each new PW step along the way to a high-resolution structure.

IV. Initial Distribution of the Scattering Bodies

An initial distribution of scattering bodies is created by placing a plurality of scatterers into the previously calculated envelope. The scattering bodies are then allowed to condense (i.e. rearrange) into a final distribution by repeated movements, subject to two constraints: first, the scatterers must pack as if they were hard objects, and second, they must distribute themselves to maximize the correlation with the observed Fourier amplitude data. The scattering bodies are thus hypothetical objects used to diffract hypothetical X-ray radiation and produce calculated Fourier amplitudes. In addition, the scattering bodies possess "packing" properties such as a fixed shape and size. Scattering bodies can therefore be described in terms of physical characteristics such as a radius and a scattering cross-section. As described below, the number and properties of the scatterers depend on the current resolution of the envelope and the properties of the protein envelope within the asymmetric unit of the crystal.

During the condensation process, no scattering body can move to occupy the space already occupied by another scattering body; in other words, two scattering bodies can approach each other only until their surfaces touch. Without this physical limitation, the scattering bodies would be able to condense into the same small region in the envelope. In preferred embodiments, the requirement that no two scattering bodies can occupy the same space is initially relaxed in each PW step, as will be explained below.

The space occupied by a scattering body is determined by an outer surface which can take on many shapes and sizes. In a preferred embodiment, a scattering body is a sphere, ellipsoid, cube, tetrahedron, etc. In more preferred embodiments, the scattering bodies are spheres having a predefined radius. It should be noted that the dimensions of the scattering bodies will often vary from one PW step to another.

The scattering bodies cannot, in theory, provide a phase description of the macromolecule to a resolution better than their intersphere collision distance (e.g., 3 Å for spheres having a 1.5 Å radius). In practice, they typically cannot produce a phase description better than three times their intersphere collision distance. Thus, the scatterers usually should not have a diameter larger than about ⅓ of the desired resolution. (The resolution at any given PW step is equal to the resolution of the reflection being phased.) In a most preferred embodiment, each scatterer has a diameter of preferably 1/6 to ⅓ of the resolution desired for the current PW step. Thus, if the current PW step is designed to provide an envelope having a resolution of 12 Å, the scatterer diameter will preferably lie between 2 and 4 Å. In more preferred embodiments, the scatterer diameter will lie between about ¼ and 1/5 of the desired resolution for the current PW step.

Although the scattering bodies are preferably spherical having a fixed radius, for purposes of calculating Fourier amplitudes, each is treated as a point scatterer having a scattering factor of unity, thus permitting easier evaluation of the Structure Factor Equation. When the length of time required to evaluate the Structure Factor Equation is not an issue, however, the scatterers may have scattering profiles that approximate the spatial distribution of a real atom, such as a Gaussian profile or a Normal profile. Of course the Structure Factor Equation becomes more complex and requires more computation time for these more complex scattering profiles.

The number of scatterers distributed within the protein envelope depends on many factors, such as the radii of the scatterers, the number of non-hydrogen atoms in the envelope, the packing fraction of the macromolecule in the asymmetric unit, and, most importantly, the resolution of the experimentally collected reflections used in the current PW step. In a preferred embodiment, the number of scattering bodies is calculated by first determining the maximum number of spherical scattering bodies, $N_{max}$, that will fill the volume occupied by the macromolecule fraction of the asymmetric unit. Some fraction of $N_{max}$ defines the total number of scatterers to be distributed within the macromolecule envelope. This fraction is chosen to provide enough free space within the macromolecule portion of the asymmetric unit to allow the scatterers to explore various desirable arrangements during the condensation process.

To determine $N_{max}$, the volume of the asymmetric unit occupied by solvent (and hence its inverse, the macromolecule) must be determined. The exact percentage of solvent can be estimated with reasonable accuracy, as is known in the art. In the case of proteins, enzymes, polymeric nucleic acids etc., the primary sequence may be used to estimate the volume occupied by the macromolecule. A typical protein will have a macromolecule fraction of about 0.6 (i.e., 40% of the unit cell volume is occupied by solvent). Multiplying the macromolecule fraction in the crystal by the total volume of the asymmetric unit gives the total volume occupied by the macromolecular envelope of the asymmetric unit. With this knowledge and the maximum packing density of the scatterers, $N_{max}$ can be determined.

For a plurality of spherical scatterers having the same radius, the theoretical value for the maximal random packing fraction is about 0.6. That is, spheres randomly packed to maximize their density will fill 0.6 (i.e., 60% of the volume). Thus, the number of spherical bodies needed to maximally fill the macromolecule space of a typical protein with 40% solvent is given by the following expression:

$$N_{max} = (0.6)(0.6)\frac{V_{asymmetric\ unit}}{V_{sphere}} = 0.36 \frac{V_{asymmetric\ unit}}{\left(\frac{4}{3}\pi r^3\right)}$$

where r is the radius of each sphere. Of course, if $N_{max}$ spheres were to fill the macromolecular envelope, they would lie in a tightly packed arrangement without any substantial translational freedom. Thus, in order that the scattering bodies be mobile, their total number must be significantly smaller than $N_{max}$. In addition, the Fourier constraints impose further constraints that further decrease the number of scatterers, as described below.

In a preferred embodiment, the optimal number of scattering bodies, $N_{hs}$, is between about ⅛ and about 1/10 of $N_{max}$. In a more preferred embodiment, the number of scattering bodies is between about ⅛p0 and about 1/6 of $N_{max}$. Since $N_{max}$ (from the above equation) depends on the radius of the sphere, this radius or equivalently its diameter (i.e., twice radius) needs to be pre-determined. This value for the sphere diameter is preferably chosen to be between about ¾ and 1/6 of the desired resolution for the current phase walk step. Most preferably, it is selected to be about ⅓ of the desired resolution.

Once the number of scatterers is determined, as described above, the macromolecular envelope is filled with the appropriate number of scattering bodies of a predetermined radius. As mentioned above, the centers of any two spheres normally cannot approach closer than the sum of their radii. However, when the scatterers are initially loaded into the macromolecular envelope this requirement is preferably relaxed. Generally, it is preferable to distribute these scatterers close together near the region of maximum electron density within the macromolecular envelope. As will be described below, the present invention provides a grid or map that represents the calculated electron density at each position within the asymmetric unit. Preferably, the scatterers are initially loaded into only those grid blocks having the highest 5 to 20% (and preferably about 10%) of the electron density values. With this constraint, the scatterers may initially be distributed so that their centers are separated by less than the preferred value of one-third of the desired resolution for the current PW step. Thus, in this scenario or in less preferred circumstances where spheres of diameter greater than one-third of the desired resolution are used, the initially loaded scatterers will overlap somewhat.

This "high-density" initial loading is preferred because it more closely represents (in comparison to a random distribution) the arrangement of scattering centers within a true macromolecule. Although most of the scattering centers of a true macromolecular crystal are located near regions of higher electron density, some scattering centers are, of course, present in regions of lower electron density. The hard object packing constraint of the present invention forces the initially concentrated scatterers to quickly "diffuse" to these regions of lower electron density. Put another way; because the scatterers are initially packed together and because they cannot "move" into space currently occupied by another scatterer, they will naturally move apart during the initial stages of the condensation protocol.

The above discussion has referred to scatterers in the macromolecular fraction of an "asymmetric unit." However, as pointed out above, the repeating unit of interest, the unit cell, may contain multiple asymmetric units. The scatterers loaded into a single asymmetric unit are related by certain symmetry operations to the scatterers in each of the other asymmetric units within the unit cell. Thus, if the distribution of scatterers in one asymmetric unit is known, the distribution in the other asymmetric units is also known. In some embodiments, the computational resources are expended first on producing an accurate representation of the asymmetric unit, and then on constructing the unit cell from the asymmetric unit by the appropriate symmetry operations. For example, the arrangement of scattering bodies within that asymmetric unit would be used to construct the scatterer distribution in the entire unit cell by moving corresponding scatterers in the other asymmetric units. Of course the asymmetric unit in which the calculations are conducted will have boundary conditions that prevent its scatterers from occupying the spaces occupied by scatterers in an adjacent asymmetric unit.

V. Condensing Protocol For Phase Extraction

Once the initial distribution of the scattering bodies is determined, the Fourier amplitudes of this distribution are calculated by a trigonometric summation using the Structure Factor Equation. In a preferred embodiment, the following equation is used:

$$F(h, k, l) = \sum_{j=1}^{N} f_j \exp[2\pi i(hx_j + ky_j + lz_j)]$$

In other preferred embodiments, other methods for calculating the Fourier amplitudes are used. Suitable methods include, for example, Fast Fourier Transform methods (See Press et al. Numerical Recipes in C: The Art of Scientific Computing, Cambridge University Press, 1988, incorporated herein by reference for all purposes.)

The calculated Fourier amplitudes are then correlated with selected segments of the experimental data to determine the fit. Typically, the experimental data used in the correlation is restricted to include only those reflections of resolution equal to or less than that of the reflection currently being phased. Thus, if the scatterers are condensing in an envelope that has been resolved based upon the first 98 reflections (i.e., the lowest resolution 98 reflections), and the data for the 99th reflection is being phased in the current PW step, only the 99 lowest reflections from the experimental data should be used in the correlation.

In the initial PW steps (those involving the first five and preferably about the first twenty lowest resolution reflections), however, data from additional reflections will sometimes have to be used in the correlation, so that the effect of any possible scaling error between the experimental and calculated amplitudes can be avoided. (Scaling errors are very dependent on the size of the sets of data that are being overall scaled with each other. So one needs at least a few reflections to minimize the effect that a single poorly measured reflection can have on the relative scaling of the whole set of reflections.) The additional data necessary will preferably include the lowest five reflections, and more preferably about the lowest twenty reflections. After these initial PW steps, only the data from the reflection being phased (and each of the lower reflections) is used in the correlation. In later PW steps (100 to 200 or more reflections), when higher resolution data is being phased, multiple reflections may be evaluated in one PW step. It will, of course, be necessary in such cases to correlate the experimental data for all the reflections currently being phased.

Many methods exist for determining the correlation between two sets of data. In a preferred embodiment, the Pearson correlation coefficient, r, is used. The Pearson coefficient takes the form:

$$r = \frac{\Sigma(|E_e| - <|E_e|>)(E_c - <|E_c|>)}{\sqrt{\Sigma(|E_e| - <|E_e|>)^2 \Sigma(|E_c| - <|E_c|>)^2}}$$

where $|E_c|$ is the amplitude of the experimental data points and $|E_c|$ is the amplitude of the calculated points. The summations are taken over all experimental data points. A value of zero for r represents a completely random correlation, while a value of 1 for r represents a perfect correlation and $-1$ represents complete anti-correlation. Thus, to improve the fit between the experimental X-ray diffraction data set and the calculated results, the scatterers are moved to increase the Pearson coefficient.

In another preferred embodiment, the crystallographic "R-factor" correlation, R, is used to correlate the data sets (See, Blundell and Johnson). With this correlation, a closer correlation between the experimental and calculated amplitudes results in a smaller value of R (zero represents a perfect correlation, while 60 to 100 represent random correlation). Thus, to maximize the fit between the two data sets, R is minimized. Other methods of correlating the two data sets are well known and will be apparent to those skilled in the art.

In a preferred strategy for modifying the scatterer distribution, one of the $N_{hs}$ scattering bodies is selected and moved in a random direction. In some embodiments, however, the scattering body is not moved randomly, but rather is constrained to move more often (or exclusively) in certain favored directions. For example, in some embodiments, the scattering bodies will move parallel to one of the six directions defined by the unit cell edges. Other limits on the direction of movement will be apparent to those of skill in the art.

The distance of the movement is chosen to allow the scattering bodies to "explore" the macromolecular envelope at a particular resolution. Thus, the length of the step (as distinct from a phase walk step) is determined by parameters such as the envelope dimensions, the recent values of the correlation coefficient, the number of scattering bodies, and, most importantly, the current resolution of the envelope. In preferred embodiments, the applied step-size x varies randomly about a mean step size, $\mu$ as, for example, in a Gaussian or linear distribution. The mean step size $\mu$ will typically be about $\frac{2}{3}$rds of the current resolution. However, as will be described in detail later, this range may be extended so that, for example, a scattering body may be moved a random distance between zero and one-third the average dimension of the envelope.

Regardless of which direction and distance the scattering bodies move, they must not move into the space occupied by another scattering body. Thus, as noted above, the scatterers are treated as solid balls, having a precisely defined radius. After the move direction and distance are selected, the final position of the scatterer is checked to determine whether it overlaps with another scatterer. If so, the move is rejected and another scattering body is moved randomly, subject to the same constraint. If the scattering body is moved to a location that is outside of the asymmetric unit, it is repositioned back into the unit cell by use of the appropriate space-group dependent symmetry operator (i.e. the scattering body is "folded" back into the asymmetric unit). Of course, this move will be rejected if, upon folding back into the asymmetric unit, the scatterer bumps into another scatterer.

Upon completion of an allowable move, the scattering amplitudes for the new distribution are calculated, and the correlation coefficient is reassessed for this new distribution of scattering bodies. If the correlation coefficient is more favorable (indicating a closer fit), then the move is accepted. Otherwise the move is rejected, and the sphere is returned to its original position. In this way only moves that result in a closer fit are allowed.

The process of moving a scattering body is defined herein as a "microcycle." A microcycle is "attempted" if the movement of the body is allowed (that is, the "physical" constraint is satisfied) and the correlation coefficient is calculated. Otherwise the microcycle is "rejected." If the correlation coefficient calculated for the new distribution indicates a closer fit between the experimental data and calculated amplitudes, the move is "accepted," and a new microcycle is started. If, however, the correlation coefficient indicates a worse fit, the move is "rejected."

Figure 2:
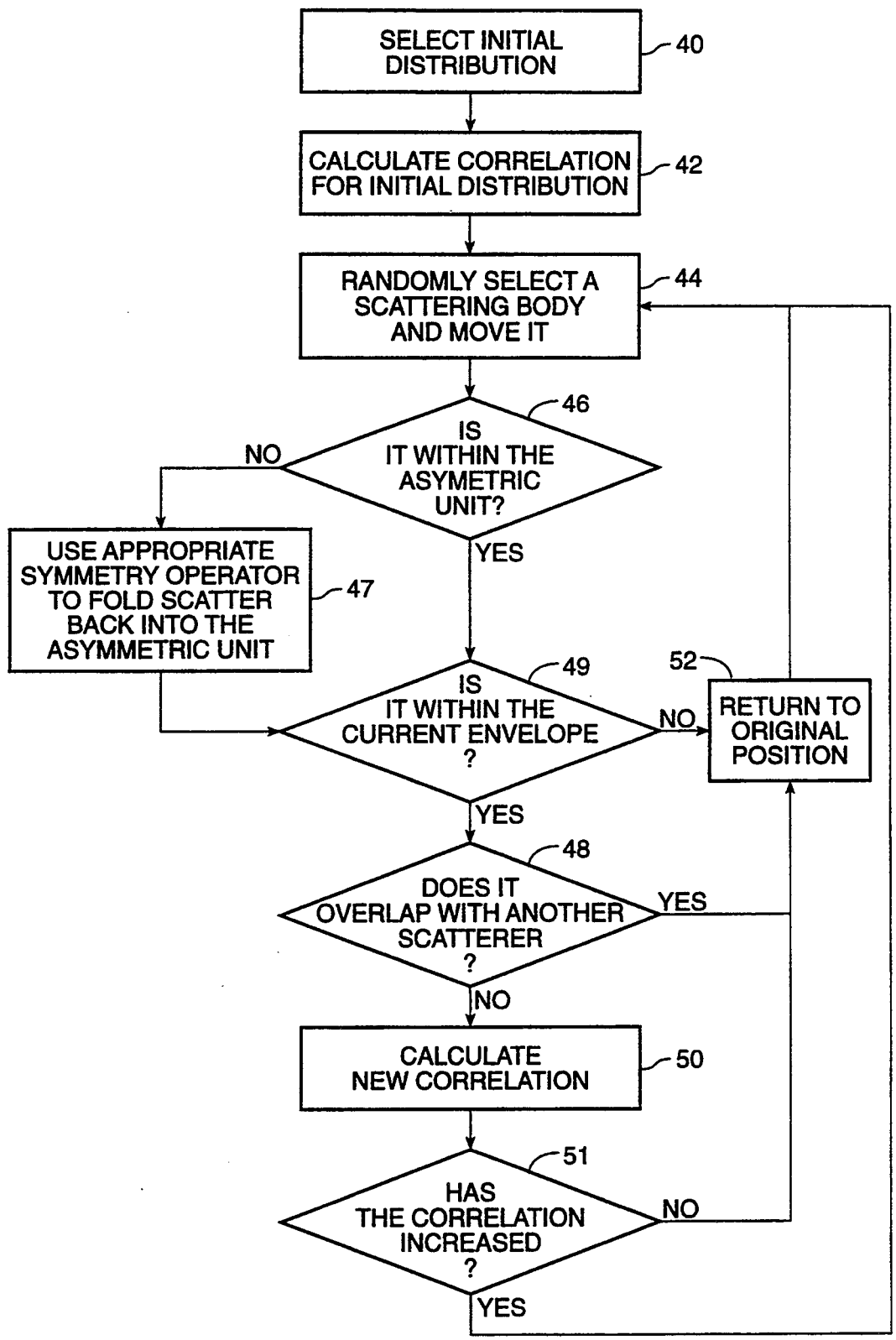
FIG. 2 is a schematic flowchart showing the features of a microcycle.

Referring now to FIG. 2, the procedures involved in each microcycle are shown schematically in a flow-chart. After the initial distribution of scatterers is selected 40 and the correlation coefficient, r, is calculated 42, one of the scatterers is randomly selected and moved 44 under the constraints described above. The new position of the scatterer is determined and if it does not overlap with another scatterer (procedures 46, 49 and 48), the correlation coefficient is calculated for this new distribution 50. If the movement criterion is violated or r decreases (indicating a worse fit), the scattering body is returned to its original position 52, and the microcycle begins again.

After the first microcycle is accepted, another scattering body is randomly selected and moved according to the previously-described constraints. In a preferred embodiment, the scattering bodies are moved by step-sizes x centered about a $\mu$ mean step-size, during each microcycle until the distribution has condensed to a stable state (i.e., when the correlation coefficient has converged to a stable environment that indicates an effective maximum correlation between the calculated and experimental amplitudes). The number of attempted microcycles as well as the number of accepted and rejected microcycles are tabulated throughout the condensation process. When 10 accepted moves occur before a total of 100 attempted microcycles have occurred, the collection of attempted moves is collectively defined as a "condensing macrocycle," and indicates that the distribution of scattering bodies, as a whole, is converging to a closer fit with the experimental data. If 10 moves have not been accepted before 100 attempted moves, the set of 100 attempted moves is defined as a "condensed macrocycle," which suggests that the distribution is in a stable environment. At this stage, the distribution of the scattering bodies is effectively maximized at the current value of mean step-size. That is, further movement of scatterers will probably not increase the correlation between the data. A set of approximately 200 consecutive macrocycles together constitute a "supercycle." In a preferred embodiment, all microcycles within a given supercycle have the same mean step-size, $\mu_q$ (i.e., each scattering body is moved the same mean distance within a supercycle). A supercycle can have less than 200 macrocycles if 40 condensed macrocycles occur consecutively, which indicates that the distribution has converged to a close fit with the experimental data using the current mean step-size that the scattering bodies are moved.

Typically, only one supercycle will be needed in any given PW step (i.e. during the condensation process for an envelope at a given resolution) to obtain a suitable correlation. In the first PW step, however, when the envelope is not well defined, it may be necessary to conduct more than one, and typically a few, supercycles. In any case, a mean step-size, $\mu$, for the first supercyle in any phasewalk step is determined in the following manner. Except for the first (or few) phasewalk steps, a preferred mean step-size, $\mu$, for the first supercycle is between about 1 and ⅓rd of the current envelope resolution, and, in a more preferred embodiment, it is about ⅔rds of the current envelope resolution. While these estimates for the mean step-size for the first supercycle are valid for typical phasewalk steps later in the overall process, in the very first or first few phasewalk steps, the mean step-size for the first supercycle is selected differently. Typically, for these early phasewalk steps, the mean step-size for the first supercycle is selected to be about ⅔rds of the lowest resolution reflection for the macromolecule crystal structure in question. In other embodiments, more generally, it can be in the range of ⅓ to ⅔rds of the average dimension of the envelope, or even more generally, the average dimension of the asymmetric unit.

In any case, having selected the mean step-size for the first supercycle in a give phasewalk step, this mean step-size is typically decreased by a factor of ⅔rds before the next supercycle. Thus, preferably, the mean step-size during a given supercycle q, is related to the mean step-size of the previous supercycle q-1, according to the following equation:

$$\mu_q = \tfrac{2}{3}\mu_{q-1}$$

To compensate for such a large step size decrease and to ensure a smooth and continuous condensation, the actual applied step size for a particular move during supercycle q, $x_q$, is preferably allowed to randomly vary about the mean step-size for that supercycle, $\mu_q$. Thus, for example, during each supercycle, the applied step size, $x_q$, is chosen randomly, with uniform probability, within the range defined by the following equation:

$$5/6\ \mu_q \leq x_q \leq 5/4\ \mu_q$$

where $\mu_q$ is the mean step size during supercycle q. Alternatively, the step size can vary in a gaussian or other suitable distribution about the mean step size. For the first or first few phasewalk steps, the last supercycle occurs when the systematically decreasing mean step-size, $\mu_q$, reaches a value that is ⅔rds of the highest resolution data used in computing the r value for maximization. In other embodiments, this condition can be relaxed to a range that is between this highest resolution and ⅓ of this highest resolution. For later phasewalk steps, typically only one supercycle is conducted. However, in other embodiments, two or three further supercycles with decreasing $\mu$ values can be conducted.

These methods of varying the step-sizes are designed to perform large random movements in the initial supercycle(s) that explore the envelope at a given resolution, while the smaller moves in the final supercycle(s) sample the calculated envelope and experimental Fourier data more finely. Not unexpectedly, step-sizes smaller than about a third of the highest resolution used in calculating the fit contribute little to the final outcome.

This whole process of phasewalk steps, that each comprise one or more supercycles, will result in phases predicted to a desired final resolution, K. The whole process can be described as "phasewalking to a desired resolution of K".

The computing time for this phasewalking procedure is modest-many macromolecular problems require roughly on the order of an hour of computer time on a mainframe computer such as a VAX 8550, produced by Digital Equipment Corporation of Maynard, Mass. Other computers are suitable for practicing the invention, the choice of which will be apparent to one skilled in the art, as described above.

Many of the parameters used with the phasewalking protocol of the present invention may be varied. For example, in other embodiments of the invention, the numbers of individual microcycles in a macrocycle, or the number of macrocycles in a supercycle are modified. The constraint that must be observed is that the number of microcycles must be sufficient to sample a sufficient number of allowable moves during the condensing procedure. In other embodiments, the radii of the scattering bodies are modified concurrently with modification of the step-sizes subject to the constraints imposed by the resolution of the current envelope.

VI. Extracting Phases for Structure Factors

As noted, the method of the present invention can be extended to high-resolutions by a step-wise application of the above condensing protocol to successively more refined envelopes. After the condensed arrangement of scatterers has been determined, an inverse Fourier transform is taken to calculate the amplitude and phase angle for the reflection of interest. This may be accomplished by summing the contributions of each scatterer (defined by its three-dimensional cartesian coordinates) according to the structure factor equation for the reflection of interest (given by its h,k,l location on the detector). The resulting summation gives the structure factor in the form of $F(h,k,l) = |F|\exp[i\phi]$, where $|F|$ is the magnitude of the structure factor and $\phi$ is the phase.

Typically, five or more independent runs will be conducted to determine the phase of the subject reflection. Thus, the scatterers are condensed from at least 5 different random starting distributions. In each case, the final distribution is used to calculate the phase of the reflection of interest. The results of the runs are compared to identify proper phases. Ideally, each of the five or more runs will produce substantially similar or identical phases. As an internal check on the calculated phases, the magnitudes of the calculated structure factors can be compared with the magnitudes of the experimentally obtained structure factors. If the two magnitudes are substantially different, the calculated phase may be suspect. Typically, for a "good" fit, the calculated and experimental magnitudes can be expected to agree to within about 30%.

If the phases of the various runs do not agree, and/or the calculated structure factor amplitudes do not agree with the experimental structure factor amplitude, the phase of the subject reflection may have to be disregarded in the overall method. In some instances, the experimental data for that particular reflection will be weak, and therefore unreliable. If the data from any reflection is weak or otherwise suspect, then the next higher reflection should be evaluated. In general, however, as many of the lowest-resolution reflections as possible should be used. Errors should not be introduced, especially in the early stages of the process because they will, as noted above, propagate as the method continues.

Since about 20% of the lower reflections for most macromolecule crystals are "centric", the lowest resolution reflections can be phased very accurately at the early stages. The structure factors of centric reflections (e.g. the 0,0,1, 0,1,0, etc. the hkl planes that are causing the reflections) usually have phases of either 0° or 180°. Thus, the phase angles for many lower resolution reflections can be accurately rounded to 0° or 180°.

The above discussion has described embodiments in which a single phase is calculated for each new envelope. This conservative approach is typically preferred because there is less chance for an erroneous phase to be introduced into the method. If, however, the experimental data and the calculation method used for a group of similar resolution reflections is known to be trustworthy, then multiple phases can safely be calculated for a new envelope. This will substantially speed the process to attain a high-resolution image.

VII. Refining Higher-Resolution Envelopes

After the new phase or phases are determined, it (or they) are used in conjunction with the previously phased structure factors to obtain an electron density map of the macromolecule within the asymmetric unit. One of the map's contours of equal electron density will define the new higher resolution envelope for the subsequent PW step as described below. The electron density map is created from the Electron Density Equation presented above:

$$\rho(x, y, z) = \frac{1}{V} \sum_{h,k,l=-\infty}^{\infty} F(h, k, l) \exp[-2\pi i(hx + ky + lz)]$$

The electron density at each spatial coordinate (x,y,z) on the map is determined by summing structure factor contributions for each phased reflection according to the above equation. Of course, only those structure factors previously phased can be used in this expression, as the phases of the higher resolution structure factors are as yet unknown. With each new PW step, one or more additional structure factors are added to the summation, thus increasing the resolution of the image.

After the new electron density map has been prepared, scatterers are placed in regions of high electron density. Typically, the asymmetric unit is divided into a grid of perpendicular lines, defining boxes that can each accommodate a single scatterer. As the resolution increases in succeeding PW steps, the fineness of the grid should also increase to allow for additional scatterers per unit volume. The grid will preferably accommodate three scatterers (and generally in the range of 1 to 6) per one-dimensional unit of the current resolution.

Each element of the grid so created has an associated electron density value. Scatterers are placed only in those grid elements having certain predefined high electron density. The exact percentage of grid elements in which scatterers are placed will depend upon the estimated macromolecular fraction in the asymmetric unit and can be expected to be exactly, or close to, that fraction. For instance, the macromolecular fraction is estimated to be about 45%, scatterers will be placed in a series of trial contours in the range of 5–95% in steps of 5–10%. For each trial contour, the appropriate percentage of the grid elements will be occupied by scatterers and subsequently, the Fourier amplitudes of the arrangement of scatterers can be computed as described above for the condensing protocol. The pattern of Fourier amplitudes so calculated is then correlated with the experimental X-ray diffraction data. The trial contour that has the highest correlation with the data defines the new envelope contour for the next PW step. Typically, the arrangement exhibiting the best correlation will have scatterers occupying a percentage of the grid elements that is near the predicted percentage of the asymmetric unit occupied by the macromolecule.

As an example, the solvent may be expected to occupy 55% of the asymmetric unit volume (and the macromolecule would occupy the remaining 45%). The scatterers might initially be placed in many more grid elements than would be expected for the macromolecule. After the Fourier amplitudes and correlation for this arrangement are calculated, some of the scatterers would be removed and a new correlation made. Thus, for example, the first scatterer collection may cover about 80% of the grid, next 70%, then 60%, then 50%, then 45%, 40% and finally 30%. The correlation for one of these collections (which defines the new envelope) will be greater than the others. Typically, it should be the distribution occupying about 45% of the grid. Of course, this will not always be the case, as the overall expected estimate for the macromolecular fraction will not always be accurate for the current resolution. In some cases, it will be necessary to use additional scatterer distributions to precisely identify the maximum. Thus, for example, if the distributions occupying 45% and 50% of the map elements gave similar correlations, additional runs might be conducted for 46% and 48%.

After the new envelope is identified, the next PW step begins. Thus, an initial distribution of scatterers is placed within the new envelope, preferably with "high-density initial loading," and condensed as before. Of course, the data used in the correlation will include the next higher resolution reflection for which a phase is desired. Next, the phase is calculated for the reflection of interest and a new, higher resolution envelope is determined as described. This entire process (condensing, phasing, and refining the envelope) is repeated several times, stepping through reflections sequentially, each time obtaining a phase for the next highest reflection. The process is stopped when an envelope having the desired resolution is obtained.

After 100 to 200 reflections have been used to calculate new envelopes, it will often be desirable to step in larger increments (i.e. more than one reflection will be phased in a given PW step). This will expedite the procedure, often without introducing significant new error. In addition, any such new errors are likely to be due to the weaker reflections. Thus, the risk of introducing error at these larger PW steps can be minimized by considering only the stronger reflections. Preferably, the larger PW steps will be done in increments of up to about 15% of the total number of reflections phased thus far. For instance, if the method had reached 200 reflections, it might be expedient to jump to 230 reflections for the next iteration. Of course, other PW step sizes might be used, but preferably the jump will traverse no more than 100% of the current reflections. More preferably not more than about 30%, and most preferably, not more than about 15%.

Ultimately, an envelope is attained having the desired predetermined resolution. The features of the macromolecule can then be displayed by a variety of techniques well known in the art. Direct visualization of the various resolution envelopes is optionally performed on a display device using suitable molecular graphics computer software. Methods for displaying the final distribution are well known in the art and include the use of computer graphics software such as FRODO, HYDRA, McIMDAD, MIDAS, MOGLI. Visualization of the macromolecular envelope shows features at the resolution of interest. For proteins, structural motifs such as inter-domain clefts and other prominent surface indentations, are typically observed at low-resolution. At higher resolution, sheets, helices, side chains, and, ultimately, atoms may be observed.

The resulting image can then be viewed on a display monitor of a type commonly used on terminals, personal computers, workstations, etc. In addition, the macromolecule image can be outputted in various forms, such as a page printout or a projection on a screen. Other methods and apparatii for displaying and outputting the final macromolecule image will be readily apparent to those of skill in the art.

All of the computational procedures leading to the high-resolution envelope can be implemented on one or more appropriately programmed digital computers or other apparatus for carrying out rapid calculations.

VIII. Examples

Example 1

For this example, the structure of the protein calmodulin was determined according to the method of this invention. Calmodulin is a 143 amino acid protein that occupies about 43% of the asymmetric unit volume. Thus, the envelope contour level (i.e., the percentage of the electron density distribution occupied by the macromolecule) should be centered about 43%, varying somewhat depending upon the resolution considered. There are eight asymmetric units in the calmodulin unit cell, and, therefore, eight symmetry operators. The space group is C 2 2 2, with the following unit cell constants: a=33.39 |, b=87.2 Å, c=127.86 Å, alpha=90°, beta=90°, and gamma=90°. The solvent fraction of the unit cell is approximately 57%.

As pointed out above, the lower resolution reflections must often be phased in groups, rather than one at a time, to avoid scaling discrepancies. In this example, the lowest ten reflections were phased in three PW steps. In each PW step, the experimental structure factors for all ten reflections were used in the condensing protocol, but only certain of these reflections were phased. In the first PW step, the strongest four reflections were phased. In the second PW step, the next strongest two reflections were phased. Finally, in the third PW step, three of the four remaining reflections were phased. In conducting these three PW steps, it was determined that one of the reflections was too weak to provide a sufficiently accurate phase. Thus, it was not considered in further steps.

For this example, the initial crude envelope (in which the first phasewalk step was performed) was generated by the method described in U.S. patent application No. 831,258, which was previously incorporated by reference herein.

The grid resolution for this envelope - and all further envelopes - was chosen to be ⅓ of the current phasing resolution. Because the first ten lowest reflections were used in the first three PW steps, the highest resolution reflection among these was used to calculate the grid space. That reflection turned out to have a 30 Å resolution, resulting in a 10 Å grid resolution (the resolution of the reflections varied from 127.9 Å to 30.0 Å). The number of scatterers used in each PW step, $N_{hs}$, was chosen to be 1/6 of $N_{max}$. The sphere diameters were chosen to be ¼ of the current resolution. Thus, since the first three phasewalk steps had a highest-resolution of 30 Å, the sphere diameters where chosen to be approximately 7 Å.

Although the ten lowest resolution reflections were used in the condensing protocol of the first phasewalk step, only the four strongest reflections were phased. These four phases were used to construct a higher resolution envelope, which was, in turn, used to phase the next two strongest reflections. Thereafter the six phased reflections were used to construct an even higher resolution envelope to phase the remaining four reflections, one of which was discarded.

In the first PW step, five supercycles were employed during the condensation protocol. For the first supercycle, the starting mean step size was ⅔rds of the lowest resolution (i.e., 85 Å). The final supercycle was ⅔rds of the highest resolution reflection (i.e., ⅔rds of 30 Å, or approximately 20 Å). All five supercycles were employed in each of the three phasewalk steps conducted during phasing of the first ten reflections. In all subsequent PW steps, only a single supercycle was conducted, and a stepsize of ⅔rds the phasing resolution was used.

In each phasewalk step, five condensation protocols were run. For all acentric reflections, the average of the five predicted phases was retained. For the centric reflections (i.e., those having a phase of either 0° or 180°), the most popular phase of the five calculated phases was retained.

After the first ten reflections were phased (in the three phasewalk steps to 30 Å) a single phase was calculated in each phasewalk step until a resolution of 20 Å was obtained. During this part of the procedure, thirteen new reflections were phased, one of which was too weak and therefore discarded.

The phasing results to this point are presented in Tables 1 and 2. Table 1 presents the first three phasewalk steps used to phase the first ten reflections. For each reflection, a variety of pertinent parameters are presented. For example, the experimental intensity of each reflection is shown as the "true" structure factor. In addition, two phases are presented: $\phi_{predicted}$ (calculated by the present method), and $\phi_{true}$ (obtained from the previously solved structure of calmodulin). To account for the effect of the reflection strength, the phase error of each reflection was multiplied by the structure factor magnitude to obtain a weighted error. Finally, the envelope contour level used for each PW step is presented. This represents the percentage of elements in the electron density grid that are surrounded by the envelope of the current resolution.

After the first 23 reflections were treated as described above, single PW steps were taken for each reflection to 15 Å resolution. To this point data, 49 total reflections were considered, of which 45 were actually phased. These 45 reflections accounted for approximately 99.5% of the total intensity, and had a weighted mean phase error of approximately 5.1°.

After the 49$^{th}$ reflection was phased, subsequent phasewalk steps included groups of reflections. Each of these groups represented approximately 10% added intensity based on the previously phased total (and amounted to approximately 10% of the total number of reflections that had been previously phased up to that point). 149 reflections were considered until a resolu-

TABLE 1

| h | k | l | Resolution (Å) | $\|F_{true}\|$ | $\phi_{true}$ | $\phi_{predicted}$ | $\|\Delta\phi\| = \phi_{error}$ | Weighted Error $F_{true} \times \phi_{error}$ | Phasewalk Step No. | Envelope Contour Level |
|---|---|---|---|---|---|---|---|---|---|---|
| 0 | 0 | 1 | 127.9 | 723  | 0   | 0   | 0  | 0      | 3 | 70% |
| 0 | 0 | 2 | 63.9  | 1596 | 0   | 0   | 0  | 0      | 2 | 60% |
| 0 | 2 | 0 | 43.6  | 7552 | 180 | 180 | 0  | 0      | 1 | 80% |
| 0 | 0 | 3 | 42.6  | 3549 | 0   | 0   | 0  | 0      | 1 | 80% |
| 0 | 2 | 1 | 41.3  | 845  | 0   | 0   | 0  | 0      | 3 | 70% |
| 0 | 2 | 2 | 36.0  | 1566 | 180 | 180 | 0  | 0      | 2 | 60% |
| 0 | 0 | 4 | 32.0  | 7869 | 180 | 180 | 0  | 0      | 1 | 80% |
| 1 | 1 | 0 | 31.2  | 880  | 180 | 180 | 0  | 0      | 3 | 70% |
| 0 | 2 | 3 | 30.5  | 227  | 0   | *   |    |        |   |     |
| 1 | 1 | 1 | 30.3  | 3219 | 194 | 172 | 22 | 70 818 | 1 | 80% |

*Skipped since weak and unreliable

TABLE 2

| h | k | l | Resolution (Å) | $\|F_{true}\|$ | $\phi_{true}$ | $\phi_{predicted}$ | $\|\Delta\phi\| = \phi_{error}$ | Weighted Error $F_{true} \times \phi_{error}$ | Phasewalk Step No. | Envelope Contour Level |
|---|---|---|---|---|---|---|---|---|---|---|
| 1 | 1 | 2 | 28.0 | 1683 | 190 | 188 | 2  | 3366   | 4  | 60% |
| 0 | 2 | 4 | 25.8 | 1822 | 0   | 0   | 0  | 0      | 5  | 40% |
| 0 | 0 | 5 | 25.6 | 4462 | 0   | 0   | 0  | 0      | 6  | 50% |
| 1 | 1 | 3 | 25.2 | 1361 | 332 | 334 | 2  | 2722   | 7  | 50% |
| 1 | 1 | 4 | 22.3 | 760  | 7   | 312 | 55 | 41 800 | 8  | 50% |
| 0 | 2 | 5 | 22.0 | 5857 | 180 | 180 | 0  | 0      | 9  | 50% |
| 1 | 3 | 0 | 21.9 | 498  | 0   | *   |    |        |    |     |
| 0 | 4 | 0 | 21.8 | 3970 | 180 | 180 | 0  | 0      | 10 | 50% |
| 1 | 3 | 1 | 21.6 | 2101 | 3   | 23  | 20 | 42 020 | 11 | 50% |
| 0 | 4 | 1 | 21.5 | 284  | 180 | 180 | 0  | 0      | 12 | 50% |
| 0 | 0 | 6 | 21.3 | 211  | 0   | 0   | 0  | 0      | 13 |     |
| 1 | 3 | 2 | 20.7 | 2477 | 39  | 44  | 5  | 12 385 | 14 | 50% |
| 0 | 4 | 2 | 20.6 | 1398 | 180 | 180 | 0  | 0      | 15 | 50% |

*Skipped since somewhat weak and all 5 predictions did not cluster together.

A summary of the first three PW steps follows. The total amplitude of the ten reflections considered was 28,026 (arbitrary units) having a total absolute phase error of 22° and a total weighted error of 70,818. Since only nine of the ten reflections were actually phased, the total phased intensity was 99.2% of the total intensity to 30 Å resolution. The absolute mean phase error was 2.4°, the weighted mean phase error was 2.5°, and the median phase error was 0°.

Of the thirteen reflections considered in the next phasewalk steps to 20 Å resolution, twelve were actually phased as shown in Table 2. Together with the reflections considered in Table 1, a total of 23 reflections were considered to 20 Å resolution. These reflections represented a total amplitude of 54,910 and a total absolute phase error of 106°. The total weighted phase error was 169,745. Twenty-one of the original 23 reflections were phased, representing phased intensity of 98.7% of the total intensity to 20 Å resolution. To this point, the absolute mean phase error was 5.0°, the weighted mean phase error was 3.1° and the absolute median phase error was 0°.

tion of 10 Å was obtained. Of these reflections, only about 91% of the total intensity was phased. This is due, in part, to the larger steps which cause more reflections to be suspect. The weighted mean phase error to 10 Å was approximately 9.2°.

After the first 149 reflections were treated as above, still larger phasewalk steps were employed. Each new phasewalk step treated a number of reflections equal to approximately 20% of the total prior reflections phased. Following this procedure, after 560 reflections were treated a resolution of 6 Å was obtained. At this point only approximately 79% of the total reflection intensity was phased. The total weighted mean phase error to this point was 24°.

Example 2

This example demonstrates how the method of this invention may be used with another commonly used crystallographic technique, heavy-atom replacement. Data from a "mock" heavy-atom replacement experiment was used in conjunction with the method of this invention to quickly determine the locations of the heavy-atoms on the protein.

In this example, the same calmodulin solved structure used in the first example was treated. The solved structure was "mock" derivatized with four samarium atoms located at four asparagin residues (samarium preferentially binds to asparagine residues) in each calmodulin molecule. Because each asymmetric unit contains a single calmodulin molecule, there should be four heavy-atom peaks in a single asymmetric unit of an electron density map. To accentuate the positions of the heavy-atoms against the background of the protein, a "difference" electron density map was prepared. This map can be viewed as a subtraction of the underivatized calmodulin electron density distribution from the heavy-atom derivatized calmodulin electron density distribution.

Mock heavy-atom amplitude data was obtained from the structure factor equation as described above. To allow for a very generous experimental error in data collection, a 2% mean random error was superimposed on the calculated amplitude data. A difference Fourier amplitude pattern was then calculated as well known in the art (see Blundell-Johnson, previously incorporated by reference).

$$|F_{diff}| - |F_{heavy+protein}| - |F_{protein}|$$

From this Fourier difference, a true structure factor difference, $F_{diff}$, can be obtained from the phases predicted by the present invention. Thus, the following equations may be used to generate an electron density map indicating the relative locations of the heavy-atoms in the asymmetric unit.

$$F_{diff} = |F_{diff}| \exp[i\phi_{predicted}]$$

$$\rho_{diff}(x, y, z) = \frac{1}{V} \sum_{h,k,l=-\infty}^{\infty} F_{diff}(h, k, l) \exp[-2\pi i(hx + ky + lz)]$$

Figure 3A:
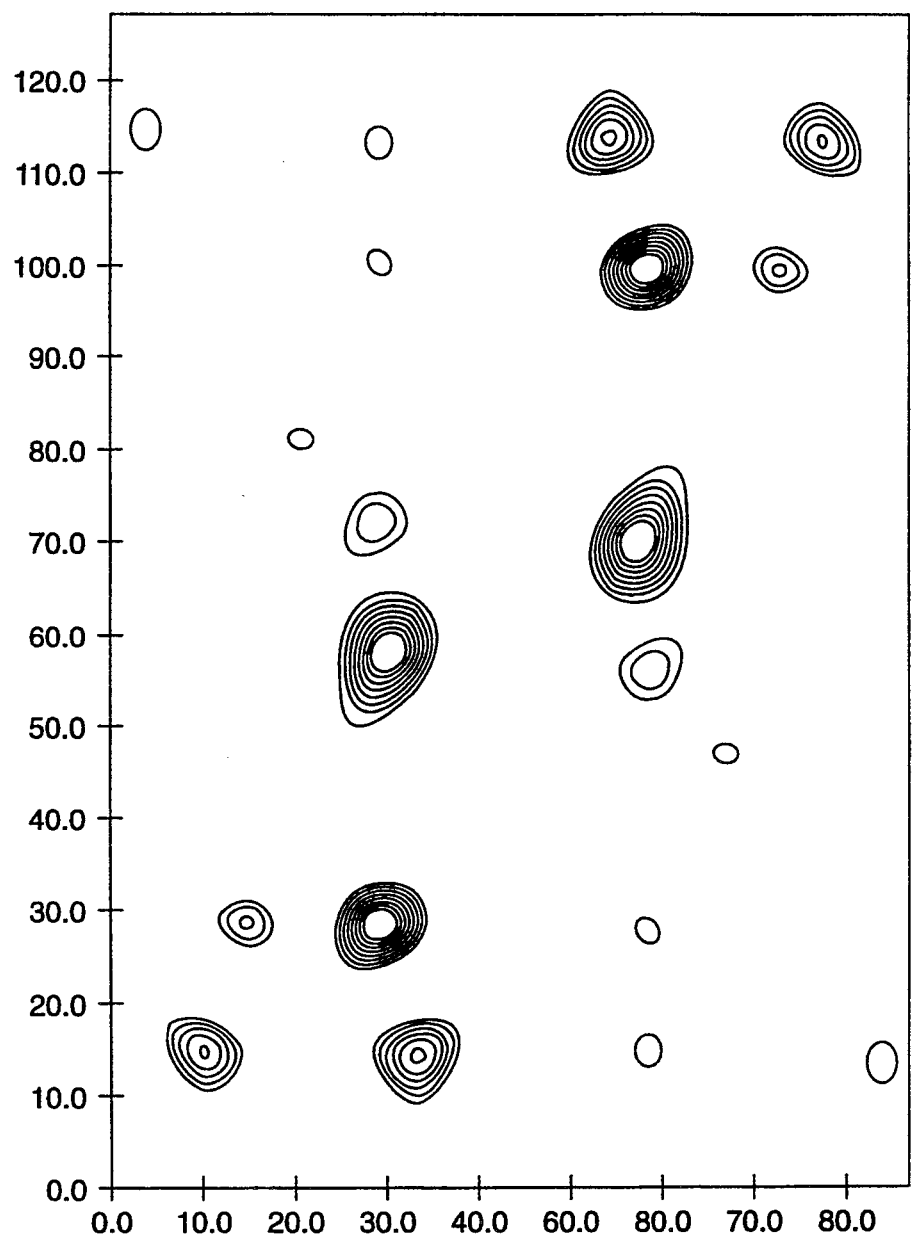
FIG. 3a is a contour plot of the electron density difference between the envelope of a heavy-atom doped protein and the undoped version of the protein.

The electron density map resulting from the above equations is presented in FIG. 3a. The positions of the samarium atoms in the unit cell are clearly shown as the raised (generally circular) regions on the electron density contour map.

Figure 3B:
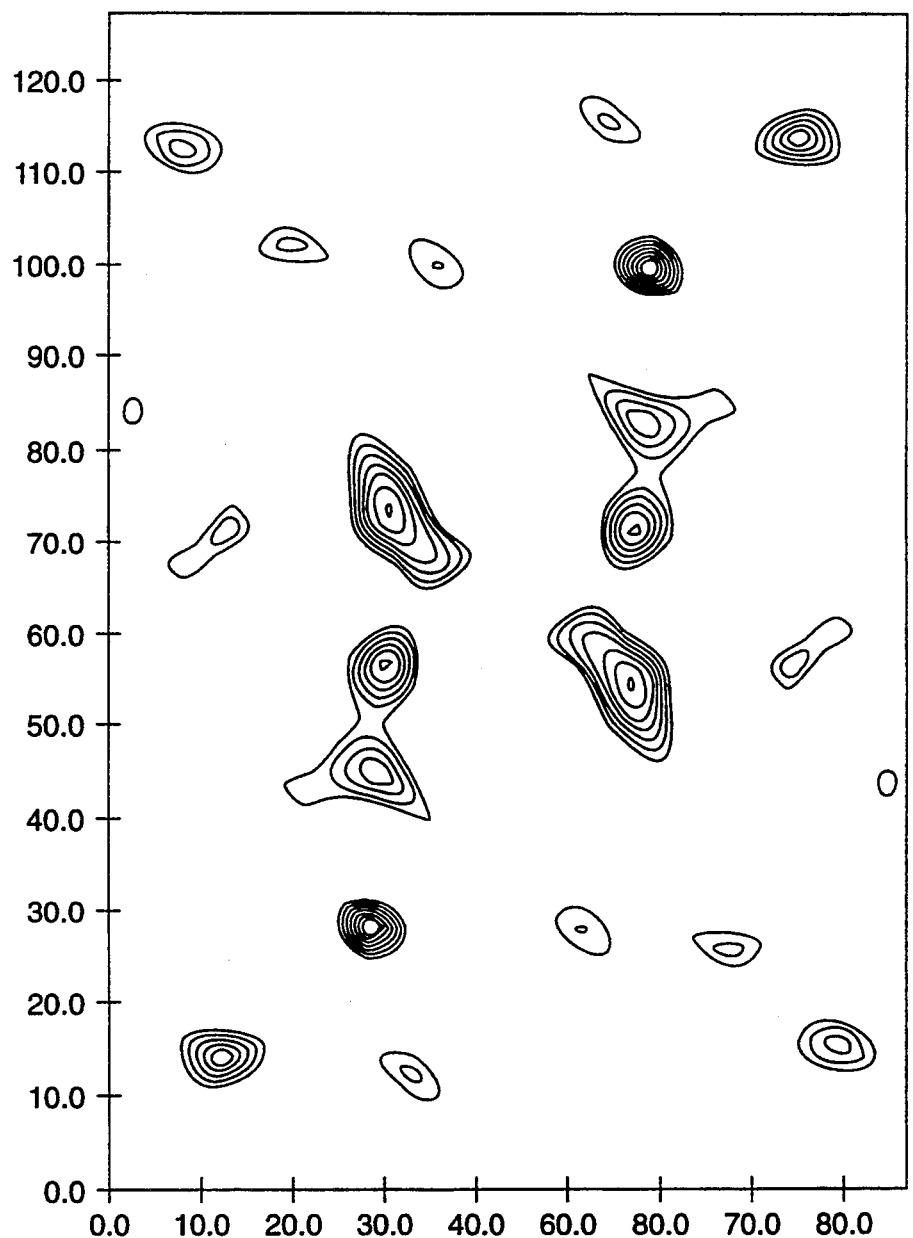
FIG. 3c is a contour plot of an undoped protein envelope substracted from a heavy-atom doped protein envelope as shown in FIG. 3a but calculated with "perfect" experimental data and the phases calculated from a previously solved structure.

For comparison, a similar map was made using perfect data (without the 2% error introduced) and the "true" phases, $\phi_{true}$ determined from the previously solved calmodulin structure. FIG. 3b represents the electron density contours from this calculation. It can be seen that the raised contours, corresponding to the locations of the samarium atoms, corresponds very strongly with those of FIG. 3a. Thus, the phases predicted by the present invention, accurately describe the number (i.e., 4) and position of the Samarium atoms on a suitably derivatized calmodulin molecule. It should be noted that Samarium is a relatively weak heavy-atom scatterer.

It should also be noted that the number of heavy-atoms binding to the protein can be determined by the technique. By simply calculating the electron density within the asymmetric unit of interest, the number of peaks can be readily seen. FIGS. 3a and 3b present a plane spanning more than the region occupied by a single asymmetric unit because the three-dimensional character of the data cannot be adequately represented by a two-dimensional plot. Thus, a larger two-dimensional cross section is provided and more than four peaks appear.

IX. Other embodiments

Other embodiments are embraced within the present invention. For instance, substantially any crystalline molecule having uniformly diffracting voids within the unit cell can be modeled by the methods described herein. Examples include the modelling of the electron density of polymeric nucleic acids, such as DNA or RNA fragments, as well as nucleic acid-peptide complexes, virus particles and the like.

Other methods for maximizing the correlation between the experimental data and the calculated amplitudes include the downhill simplex method, direction-set methods (such as Powell's method), conjugate gradient methods (such as the Fletcher-Reeves and Polak-Ribiere algorithms), variable metric methods (such as the Davidon-Fletcher-Powell algorithm), simulated annealing, random-walks, and the like. Other methods that maximizes a correlation between the calculated amplitudes and the experimental data can be used.

Moreover, other problems can be reformulated in a manner analogous to that presented above. Such as the determination of three dimensional structures using electron microscopy. In another preferred embodiment, the selection of the point scatterers to be moved is not random. For example, the selected point scatterer is the one having the largest increase in the correlation between the changed distribution and the experimental data. In another preferred embodiment, the selected point scatterer is not moved in a random direction, but in a direction corresponding to a predetermined algorithm. For example, the direction is selected to effectively maximize the increase of the correlation between the distribution and the experimental data.

Moreover, in other embodiments, a plurality of point scatterers are simultaneously moved in one microcycle. The number of point scatterers that are moved simultaneously is between one and all of the point scatterers present. In other embodiments, the mean distance that a point scatterer is moved in a cycle is variable. That is, the mean distance moved is not a fixed, pre-determined distance. In a preferred embodiment, the mean move distance is randomly chosen, but constrained in a predetermined range. Alternatively, the correlation coefficient versus the mean move distance is calculated, and the scatterer is moved to maximize the correlation.

The phases obtained at various resolutions by the present invention can be used to complement or supplement other techniques as was mentioned above. For example, both the Single Isomorphous Replacement (SIR) method and anomalous scattering technique produce two possible experimental phases for each reflection. The phases obtained in the present invention can be used to correctly resolve between the two possible phases produced by either method. In addition, the techniques of this invention can be used in conjunction with the technique of non-crystallographic symmetry-based phase extension typically used in solving large virus structures. In this technique, phase extension predicts the phase of reflections one at a time, exploiting the large non-crystallographic symmetry present. The phases predicted by the present method can be used to confirm the phases progressively predicted by the phase extension. Further, the medium resolution phases progressively predicted by the present method can be used to supplement or even supplant the technique of molecular replacement when a three-dimensional structure of a homologous molecule is already available.

Techniques of the present invention can also be used to more directly expedite the heavy-atom replacement process itself. A common difficulty in this process involves searching more than 100 heavy-atom substituted macromolecules to find a few good (for example 5 such heavy-atom derivatives) and not very complicated (i.e., easy to interpret) heavy atom derivatives. The present invention assists in this process in at least two ways. First, it quickly shows whether or not a particular heavy-atom will provide useful results, and, in so doing, prevents needless waste of resources interpreting data for useless heavy-atom derivatives. Second, the method of the present invention allows the locations of the heavy-atom within the asymmetric unit to be quickly determined. This can be accomplished by "subtracting" the electron density distribution calculated for the heavy-atom substituted macromolecule from the unsubstituted macromolecule produced by the present invention. The electron density difference provides the locations of the heavy atoms within the derivative. Finally, traditionally uninterpretable heavy-atom data can in some cases be "rescued" by the present invention. The phases produced by this invention will quickly show how many heavy-atoms are substituted on a given macromolecule and their locations.

The present invention provides new methods for modelling the electron density of a macromolecule in a crystal lattice. It is to be understood that the above description is intended to be illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

What is claimed is:

1. A method for constructing an image of a macromolecule crystal with the aid of a digital computer and the crystal's diffraction pattern, said diffraction pattern containing a plurality of reflections, each having an associated resolution, said method comprising the following procedures:
    (a) converting the diffraction pattern of macromolecule crystal into computer usable normalized amplitudes, the pattern being produced with a diffractometer;
    (b) determining from the diffraction pattern a dimension of a unit cell of the crystal;
    (c) providing an envelope defining the region of the unit cell occupied by said macromolecule in the crystal;
    (d) distributing a collection of scattering bodies within said envelope, said collection of scattering bodies having various arrangements, each of which has an associated pattern of Fourier amplitudes;
    (e) condensing said collection of scattering bodies to a condensed arrangement that results in a high correlation between a diffraction pattern and the pattern of Fourier amplitudes for said collection of scattering bodies;
    (f) determining the phase associated with at least one of the reflections of said diffraction pattern from the condensed arrangement of scattering bodies;
    (g) calculating an electron density distribution of said macromolecule within said unit cell from the phase determined in procedure f; and
    (h) displaying a graphical image of said macromolecule constructed from said electron density distribution.

2. The method recited in claim 1 wherein the procedure for condensing the collection of scattering bodies includes the following substeps:
    (i) calculating scattering amplitudes of said collection of scattering bodies and determining a correlation between the calculated scattering amplitudes and said normalized amplitudes;
    (ii) moving at least one of said scattering bodies within said envelope to create a modified arrangement;
    (iii) calculating scattering amplitudes of said modified arrangement and determining the correlation between said calculated amplitudes and said normalized values; and
    (iv) producing a final distribution of scattering bodies by repeating sub-steps (ii) and (iii) until the correlation between said calculated scattering amplitudes and said normalized amplitudes in maximized, said final arrangement of scattering bodies defining the condensed collection of scattering bodies.

3. The method recited in claim 2 wherein the scattering bodies have a predefined shape and size, and wherein during said substep of moving, no scattering bodies can move into a space occupied by another scatterer.

4. The method recited in claim 1 wherein the image defined in procedure h provides a new envelope for use in procedure d, and wherein the sequence of procedures d through h defines a phase walk step which is repeated successively, each time said phasewalk step is repeated, the phase of at least one new reflection from said diffraction pattern is determined.

5. The method recited in claim 4 wherein each new envelope defined in procedure h has a higher resolution than the previous envelope defined in procedure h.

6. The method recited in claim 4 wherein in procedure d, the collection of scattering bodies in distributed preferentially in regions having higher electron density distribution.

7. The method of claim 4 wherein a location of heavy-atoms in a heavy-atom derivatized macromolecule is determined, said method comprising the following steps:
    (a) obtaining from a diffractometer diffraction patterns for the heavy-atom derivatized macromolecular crystal and for an underivatized version of the macromolecular crystal;
    (b) conducting the method of claim 3 for the underivatized version of the macromolecule until reflections having a predefined resolution are phased;
    (c) saving selected phases of selected reflections for said underivatized macromolecule;
    (d) subtracting amplitudes of structure factors for the underivatized macromolecule from corresponding amplitudes of structure factors for the heavy-atom derivatized macromolecule to obtain amplitude differences for each structure factor;
    (e) determining a structure factor difference for selected reflections from the amplitude differences of each structure factor and the corresponding saved phases for the underivatized macromolecule; and (f) producing the electron density distribution showing the locations of the heavy-atoms from the structure factor differences.

8. The method recited in claim 1 wherein the procedure of determining the phase associated with a reflection includes summing the contributions from each of the scattering bodies in the condensed collection according to the structure factor equation for said reflection.

9. The method recited in claim 1 wherein the procedure of calculating the electron density distribution includes summing, according to the electron density equation, the contributions of each reflection for which a phase has been determined.

10. The method recited in claim 1 wherein the defined image of the macromolecule is obtained by identifying a contour of equal electron density within the electron density distribution, said contour circumscribing a scattering region which when filled with scatterers produces a pattern of Fourier amplitudes having a high correlation with said diffraction pattern.

11. The method recited in claim 1 wherein the high correlation of procedure e is determined by calculating the Pearson coefficient.

12. A method for modeling an electron density distribution of a macromolecule in an asymmetric unit of a crystal by X-ray crystallography comprising:
(a) irradiating the crystal lattice with X-rays and recording experimental X-ray diffraction data, said data containing a plurality of reflections;
(b) determining dimensions of the asymmetric unit of said crystal from said diffraction data;
(c) obtaining an envelope of the macromolecule within said asymmetric unit and distributing a collection of scattering bodies within said initial envelope, said collection of scattering bodies having various arrangements, each of which has a pattern of Fourier amplitudes;
(d) condensing said collection of scattering bodies to a condensed arrangement having a storing correlation between the experimental X-ray diffraction data and the pattern of Fourier amplitudes for said collection of scattering bodies;
(e) determining a phase associated with at least one of the reflections of said X-ray diffraction data;
(f) calculating an electron density distribution of said macromolecule within said asymmetric unit from the phase determined in procedure e;
(g) defining a new envelope of said macromolecule within said electron density distribution;
(h) performing the sequence of procedures c through g successively until a final envelope having a predetermined resolution is obtained, each time said sequence is repeated, determining the phase of at least one new reflection from said diffraction pattern; and
(g) graphically displaying said final envelope defined by the electron density distribution of the macromolecule on a display means.

13. The method recited in claim 12 wherein the procedure for condensing the collection of scattering bodies includes the following substeps:
(i) providing the diffraction data to a processor;
(ii) converting a diffraction data to a processor;
(iii) calculating scattering amplitudes of said collection of scattering bodies and determining a correlation between the calculated scattering amplitudes and said normalized amplitudes;
(iv) moving at least one of said scattering bodies within said envelope to create a modified arrangement;
(v) calculating scattering amplitudes of said modified arrangement and determining the correlation between said calculated amplitudes and said normalized values; and
(vi) producing a final distribution of scattering bodies by repeating substeps (iv) and (v) until the correlation between said calculated scattering amplitudes and said normalized amplitudes is maximized, said final arrangement of scattering bodies defining the condensed collection of scattering bodies.

14. The method recited in claim 12 wherein each new envelope defined in procedures g and h has a higher resolution than the previous defined envelope.

15. The method recited in claim 12 wherein each successive time that procedure c is performed, the collection of scattering bodies is distributed preferentially in regions of the envelope having higher electron density distributions.

16. The method recited in claim 12 wherein the procedure for determining the phase associated with a reflection includes summing the contributions from each of the scattering bodies in the condensed collection according to a structure factor equation for said reflection.

17. The method recited in claim 12 wherein the procedure of calculating the electron density distribution includes summing, according to an electron density equation, the contributions of each reflection for which a phase has been determined.

18. An apparatus for determining a high-resolution structure of a macromolecular crystal with the aid of a digital computer, said apparatus comprising:
means for converting a diffraction pattern of the macromolecule crystal into computer usable amplitudes, the diffraction pattern obtained with a diffractometer and having a plurality of reflections;
means for condensing a plurality of scatterers in an envelope defining the region of the unit cell occupied by said macromolecule in the crystal such that the condensed plurality of scatterers has an associated pattern of Fourier amplitudes having a high correlation with the diffraction pattern of said macromolecular crystal;
means for extracting the phases of one or more of said reflections from said pattern of Fourier amplitudes;
means for obtaining an electron density distribution of said macromolecule from said phases of said one or more reflections; and
means for graphically displaying an electron density distribution of the macromolecular crystal constructed from said phases.

19. The apparatus recited in claim 18 wherein the means for condensing is a digital computer.

20. The apparatus recited in claim 18 further comprising:
(a) a source of radiation that diffracts when directed onto the macromolecule crystal; and
(b) a detector for collecting an intensity versus position diffraction pattern of the macromolecule crystal.

21. The apparatus recited in claim 20 wherein the detector forms at least part of an X-ray diffractometer.

22. The apparatus recited in claim 18 wherein the means for graphically displaying displays an image of a three-dimensional density distribution of the macromolecule crystal.

23. The apparatus recited in claim 18 further comprising means for calculating a correlation coefficient between the scatterers associated pattern of Fourier amplitudes and the macromolecular crystal diffraction pattern.

24. The apparatus recited in claim 18 wherein the scatterers are spherical and the centers of any two of the spherical scatterers are separated by at least a distance equal to the sum of their respective radii.

25. A method for constructing an image of a macromolecule crystal with the aid of a digital computer and the crystal's diffraction pattern, said diffraction pattern containing a plurality of reflections, each having an associated resolution, said method comprising the following steps:

(a) converting the diffraction pattern of the macromolecule crystal into computer usable normalized amplitudes, the pattern being produced with a diffractometer;

(b) determining from the diffraction pattern dimensions of a unit cell of the crystal;

(c) providing an envelope defining a region of the unit cell occupied by said macromolecule in the crystal;

(d) distributing a collection of scattering bodies within said envelope, said collection of scattering bodies having various arrangements, each of which has an associated pattern of Fourier amplitudes;

(e) condensing said collection of scattering bodies to a condensed arrangement that results in a high correlation between the diffraction pattern and the pattern of Fourier amplitudes for said collection of scattering bodies;

(f) determining a phase associated with at least one of the reflections of said diffraction pattern from the condensed arrangement of scattering bodies;

(g) calculating an electron density distribution of said macromolecule within said unit cell from the phase determined in procedure f;

(h) from said electron density distribution, defining a new envelope defining the region of the unit cell occupied by said macromolecule in the crystal;

(i) repeating steps (d) through (h), each time with one or more previously un-phased reflections from the diffraction pattern; and (j) displaying a graphical image of said macromolecule constructed from said electron density distribution obtained after a predetermined number of repetitions of steps (d) through (g).

26. The method recited in claim 25 wherein the step of repeating steps (d) through (g), each time with one or more previously un-phased reflections from the diffraction pattern requires that the one or more un-phased reflections phased in each step are of higher resolution than the previously phased reflections.

27. The method recited in claim 25 wherein the step for condensing the collection of scattering bodies includes the following substeps:

(i) calculating scattering amplitudes of said collection of scattering bodies and determining a correlation between the calculated scattering amplitudes and said normalized amplitudes;

(ii) moving at least one of said scattering bodies within said envelope to create a modified arrangement;

(iii) calculating scattering amplitudes of said modified arrangement and determining the correlation between said calculated amplitudes and said normalized values; and (iv) producing a final distribution of scattering bodies by repeating substeps (ii) and (iii) until the correlation between said calculated scattering amplitudes and said normalized amplitudes is maximized, said final arrangement of scattering bodies defining the condensed collection of scattering bodies.

28. The method recited in claim 25 wherein in step d, the collection of scattering bodies is distributed preferentially in regions having higher electron density distributions.

* * * * *